(12) United States Patent
Abita et al.

(10) Patent No.: US 6,319,208 B1
(45) Date of Patent: Nov. 20, 2001

(54) TELEMETRIC IN VIVO BLADDER URINE MONITOR SYSTEM

(75) Inventors: Joseph L. Abita, Boyds; Jacek L. Mostwin, Baltimore; Bliss G. Carkhuff, Laurel, all of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/454,091

(22) Filed: Dec. 3, 1999

Related U.S. Application Data
(60) Provisional application No. 60/110,892, filed on Dec. 4, 1998.

(51) Int. Cl.[7] ....................................................... A61B 5/00
(52) U.S. Cl. ................................................................ 600/561
(58) Field of Search .................................... 600/561, 486, 600/488

(56) References Cited

U.S. PATENT DOCUMENTS

| | | | |
|---|---|---|---|
| 3,937,214 | * | 2/1976 | Hutchins, IV ........................ 600/305 |
| 4,281,667 | * | 8/1981 | Cosman ................................ 600/561 |
| 5,358,514 | * | 10/1994 | Schulman et al. ..................... 607/61 |
| 6,033,366 | * | 3/2000 | Brockway ............................. 600/486 |

* cited by examiner

Primary Examiner—Robert L. Nasser
Assistant Examiner—Pamela Wingood
(74) Attorney, Agent, or Firm—Carla Magda Krivak; Ernest R. Graf

(57) ABSTRACT

A telemetric in vivo bladder urine monitor system is disclosed. The invention includes a small, buoyant recorder that floats in the bladder of an animal and telemetrically relays data to an external receiver. The invention may be used in measuring urinary tract pressure in diagnosing and treating urinary tract infections, anomalous bladder contraction, etc. The invention may also be used as a monitoring system for bed wetting syndrome, artificial bladders and sphincters.

17 Claims, 4 Drawing Sheets

TELEMETRIC IN VIVO BLADDER URINE MONITOR SYSTEM

CROSS REFERENCE TO RELATED APPLICATIONS

This application claims priority from U.S. Provisional Application No. 60/110,892, filed Dec. 4, 1998, which is incorporated by reference in its entirety.

BACKGROUND OF THE INVENTION

1. Field of the Invention

The invention relates generally to sensor devices and sensing systems and, more specifically, to a system capable of in vivo telemonitoring of various properties of urine in the bladder. This monitoring system may be used, for example, in studies relating bladder pressure to urinary tract infections and anomalous bladder muscular behavior. This monitoring system applies to diagnostic and therapy measures for bed wetting syndrome, artificial bladders and sphincters.

2. Description of the Related Art

Catheters and cables are currently utilized in taking urinary tract pressure measurements. For example, U.S. Pat. No. 5,807,278 involves inserting such catheters and cables into such areas as the urethra, rectum and abdomen of the human body, which frequently causes physical discomfort to the patient, as well as restricting the patient's mobility. Accordingly, there exists a need for eliminating such catheters and cables, while simultaneously improving the means for continuously measuring urinary tract pressure, especially for ambulatory subjects in natural environments.

SUMMARY OF THE INVENTION

The invention fulfills the above-described needs and provides for an improved system for measuring urinary tract pressure. In vivo telemetric monitoring of bladder pressure aids in determining bladder events during normal activities, as well as serving as a means for notification of voiding. Further, in vivo telemetric monitoring provides new and improved data for diagnosis and modeling of conditions involving bladder pressure. The invention affords new diagnostic capabilities, such as for the homebound and institutionalized elderly, for children in their natural surroundings, and for animals in a research environment.

Accordingly, there is provided according to the present invention an in vivo telemetric bladder pressure monitoring system comprising a pressure measurement device capable of using magnetic induction telemetry and further capable of being removably insertable into the bladder of an animal, including humans and other mammals. There is also provided according to the invention, as part of the bladder pressure monitoring system, a receiver for receiving pressure data from said pressure measurement device.

In a preferred embodiment, the pressure measurement device can include a self-contained power source; a pressure sensor; at least one offset balance resistor operatively interconnected to said pressure sensor; a differential amplifier operatively interconnected to an output portion of said pressure sensor and further operatively interconnected to a discharge portion of said self-contained power source; a frequency modulator operatively interconnected to an output portion of said amplifier and further operatively interconnected to said discharge portion of said self-contained power source; an induction coil-antenna operatively interconnected to said discharge portion of said self-contained power source; an oscillator operatively interconnected to said modulator, said oscillator further operatively interconnected to said induction coil-antenna, said oscillator further operatively interconnected to said discharge portion of said self-contained power source; and a telemetry circuit operatively interconnected to said pressure sensor, said telemetry circuit further operatively connected to said discharge portion of said self-contained power source, said telemetry circuit further operatively connected to said induction coil-antenna.

In another preferred embodiment, the pressure measurement device can comprise a self-contained power source; a pressure sensor; at least one offset balance resistor operatively interconnected to said pressure sensor, a transconductance amplifier operatively interconnected to an output portion of said pressure sensor, said transconductance amplifier further operatively interconnected to a discharge portion of said self-contained power source; a pulse width modulator operatively interconnected to an output portion of said transconductance amplifier, said pulse width modulator further operatively interconnected to said discharge portion of said self-contained power source; a clock operatively interconnected to said pulse width modulator, said clock further operatively interconnected to said pressure sensor and said transconductance amplifier, said clock further operatively interconnected to said discharge portion of said self-contained power source; and an oscillator operatively interconnected to said pulse width modulator, said oscillator further operatively interconnected to said discharge portion of said self-contained power source.

In another preferred embodiment, the receiver can include a self-contained and/or external power source; at least one antenna-coil operatively interconnected to a discharge portion of said power source; at least one preamplifier operatively interconnected to an output portion of said antenna-coil, said preamplifier further operatively interconnected to said discharge portion of said power source; a signal conditioner operatively interconnected to an output portion of said preamplifier, said signal conditioner further operatively interconnected to said discharge portion of said power source; a detector operatively interconnected to an output portion of said signal conditioner, said detector further operatively interconnected to said discharge portion of said power source; a scaling amplifier operatively interconnected to an output portion of said detector, said scaling amplifier further operatively interconnected to said discharge portion of said power source; and a memory module means for data acquisition and storage, said memory module operatively interconnected to said output portion of said readout circuit.

Another preferred embodiment includes a method for determining urinary tract pressure in an animal comprising the steps of inserting a capsule into said animal's bladder, measuring said urinary tract pressure on said capsule, and removing said capsule from said animal's bladder.

Further objects, features, and advantages of the invention will become apparent from the detailed description that follows.

DETAILED DESCRIPTION OF PREFERRED EMBODIMENTS

Figure 1:
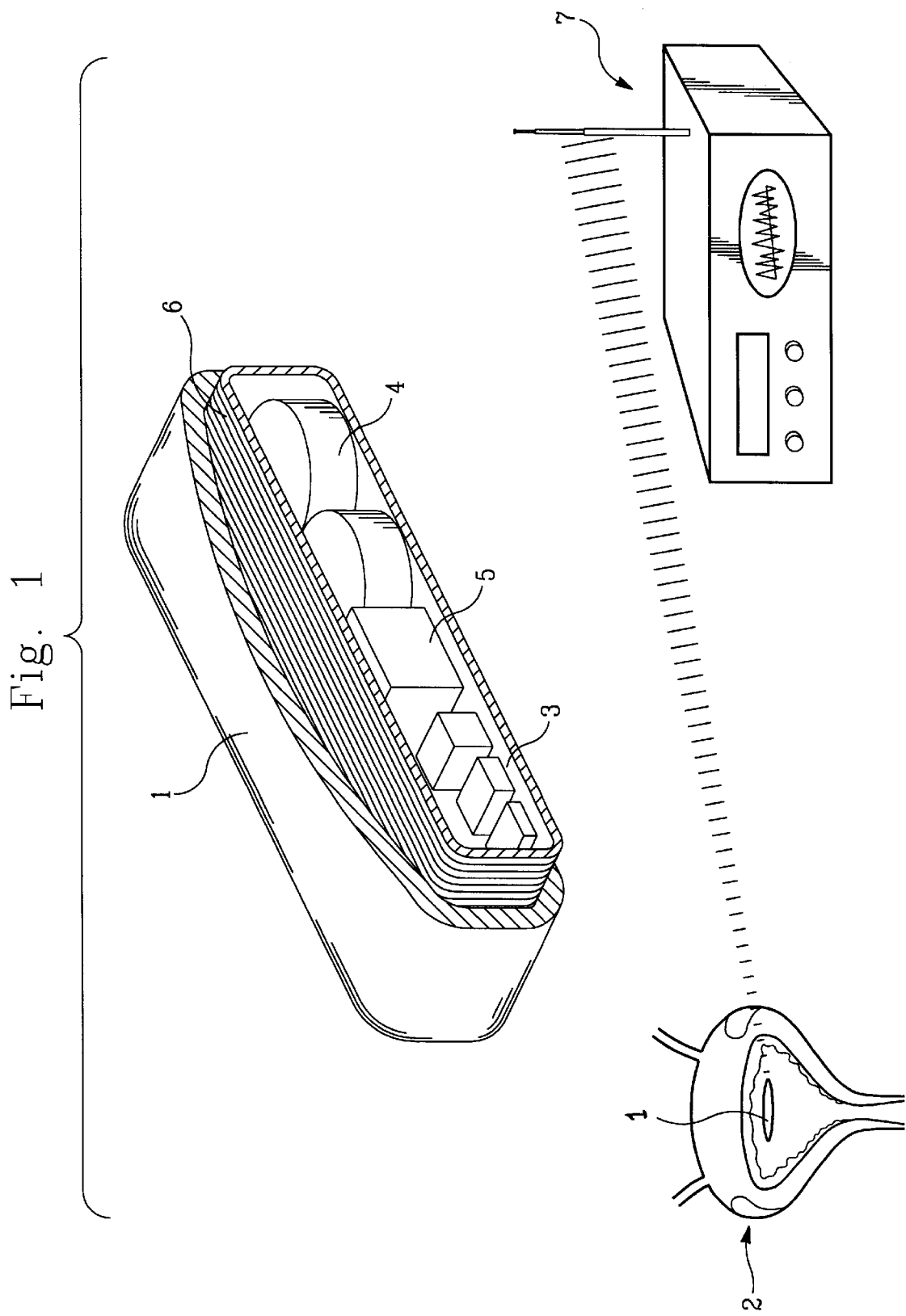
FIG. 1 illustrates a bladder urine monitor system according to the invention.

It is of significant interest to monitor pressure at various points of the urinary tract. Continuous real-time recording of pressure is important to the diagnosis of urinary tract problems and their causes, treatment and recovery evaluation. Pressure data can aid in understanding cause and effect relationships influencing urinary tract performance and health.

According to the present invention, pressure monitoring is performed using a biological parameter monitor. The biological parameter monitor can be single or multi-channel and can measure one or more biological parameter such as pressure, salinity, protein, pH, etc. of the urine. In this case the invention will be described using a single channel telemetry monitor for measuring pressure.

A pressure measurement device, as an in vivo component of the single channel telemetry pressure monitor, is very small and is buoyant so that it will float or is otherwise constrained within the bladder. The pressure measurement device is insertable and removable using a catheter-like device via the urethra of the animal or human to actively react to, in this example, pressure. The insertable measurement device's physical dimensions are approximately 4–6 mm in diameter and 10–20 mm in length. The insertable measurement device is also preferably coated with a biocompatible coating, such as a hydrophilic overcoat that becomes very slippery when wet. One example of such a hydrophilic overcoat is Lubricoat™, manufactured by Van Technologies, Incorporated (Duluth, Minn.).

The system uses magnetic induction telemetry, which involves magnetic field communication coupling of two separated (i.e., not wired together for data communication) circuits such that the magnetic field carries (telemeters) data to/from the pressure measurement device and a receiver. The receiver, as an external component of the biological parameter monitor (in this example, pressure), receives, for example, pressure measurement data, communicated via the magnetic induction telemetry link, converts the information into user readable form by way of a self contained alphanumeric display and/or a peripherally connected computer, for example. The invention employs, but is not limited to, magnetic induction telemetry similar to the communication link used in pacemakers, for example.

New diagnostic capabilities are afforded by this system. Such capabilities include urinary tract pressure monitoring, or other aspects of the urine such as salinity, etc., mentioned above, in homebound and institutionalized elderly. Also included are cases for which bedwetting can be ameliorated or eliminated in children or elderly by behavior modification according to the use and reaction to this monitor system. The system also enables urinary tract pressure monitoring, or other aspects of the urine such as salinity, etc., in children while in their natural surroundings. This is accomplished by modifying the sensor to measure these various properties. The system further provides for the determination of bladder events during normal activities, notification for voiding, and new/improved data for diagnosis and modeling.

One example of the invention is a frequency and time modulated telemetry system. This system has the advantage that signal conditioning is built into the pressure measurement device. The sensor can be of a type similar to a Wheatstone Bridge and other types commercially available, such as Motorola sensors, a Piezoresistive Strain Gauge Bridge manufactured by Lucas Nova Sensor, EXAR Silicon Microstructure sensors (Fremont, Calif.), or even custom MEMS sensors. Calibration and identification values are entered into a digital memory using an optical communications link integral to each of the monitor's measurement device and receiver. Data storage can be accomplished via digital memory media. Additionally, the invention can include a data dump feature for external high capacity data storage to a computer or other data logger. The receiver's internal data capacity may depend upon size and other aspects of available technology. The invention can incorporate multi-module memory use for increased storage capacity. In this embodiment, the pressure measurement signal data is converted to a bi-phase signal that is time division multiplexed with identification and calibration information pre-set within the pressure measurement device. Bi-phase signals are easy to synchronize to because they present an unambiguous transition for every bit. Since the speed of the bi-phase signal is determined from a voltage controlled oscillator divider, the circuit reference clock can be established from outside the body from the telemetric magnetic link carrier frequency.

Another example of the invention is a phase modulation system which phase modulates the identification information onto a FM carrier. Continuous monitoring of the pressure is an advantage of this system since the pressure signal is not interrupted by the time it would take to send the calibration information (in the above-mentioned time multiplexed case) at the expense of slightly more complexity in the telemeter (i.e., both AM and FM modulation is required). The bi-phase signal keeps the average phase constant so there is no effect on the pressure reading because it is independent of calibration phase frequency modulation. The calibration and identification values are clocked into memory using an optical communications link as in the first example.

In a preferred embodiment, the pressure measurement device can be coated with a biocompatible coating.

In another preferred embodiment, the self-contained power source of the pressure measurement device can comprise at least one battery.

In another preferred embodiment, the pressure sensor of the pressure measurement device can be a piezoresistive sensor.

In another preferred embodiment, the receiver can include a detector which is a demodulator.

In another embodiment, the receiver can include a power source comprising at least one battery.

In a further embodiment, the receiver can include a readout circuit operatively interconnected to an output portion of a scaling amplifier, said readout circuit further operatively interconnected to a discharge portion of a power source, and a readout display operatively interconnected to an output portion of said readout circuit, said readout display further operatively interconnected to said discharge portion of said power source.

In yet a further embodiment, the receiver readout display can be an alphanumeric readout display.

The pressure measurement device (PMD) of the present invention is described in more detail with reference to the figures. FIG. 1 is a cut-away view of the bladder monitor system according to the present invention that illustrates the physical appearance of the invention and how the invention resides within the bladder during in vivo use. The PMD of the present invention (1) floats or is otherwise constrained within a patient's bladder (2). The PMD contains a pressure sensor (3), a power source (4) and a telemetry circuit (5). An induction coil-antenna (inductor) (6) is wound around the PMD (1) prior to applying a biocompatible coating to the capsule (1). The telemetry circuit (5) transmits pressure data measured by the pressure sensing device (3) to an external receiver (7). Data from the receiver (7) is used in interpreting urinary tract pressure.

Figure 2:
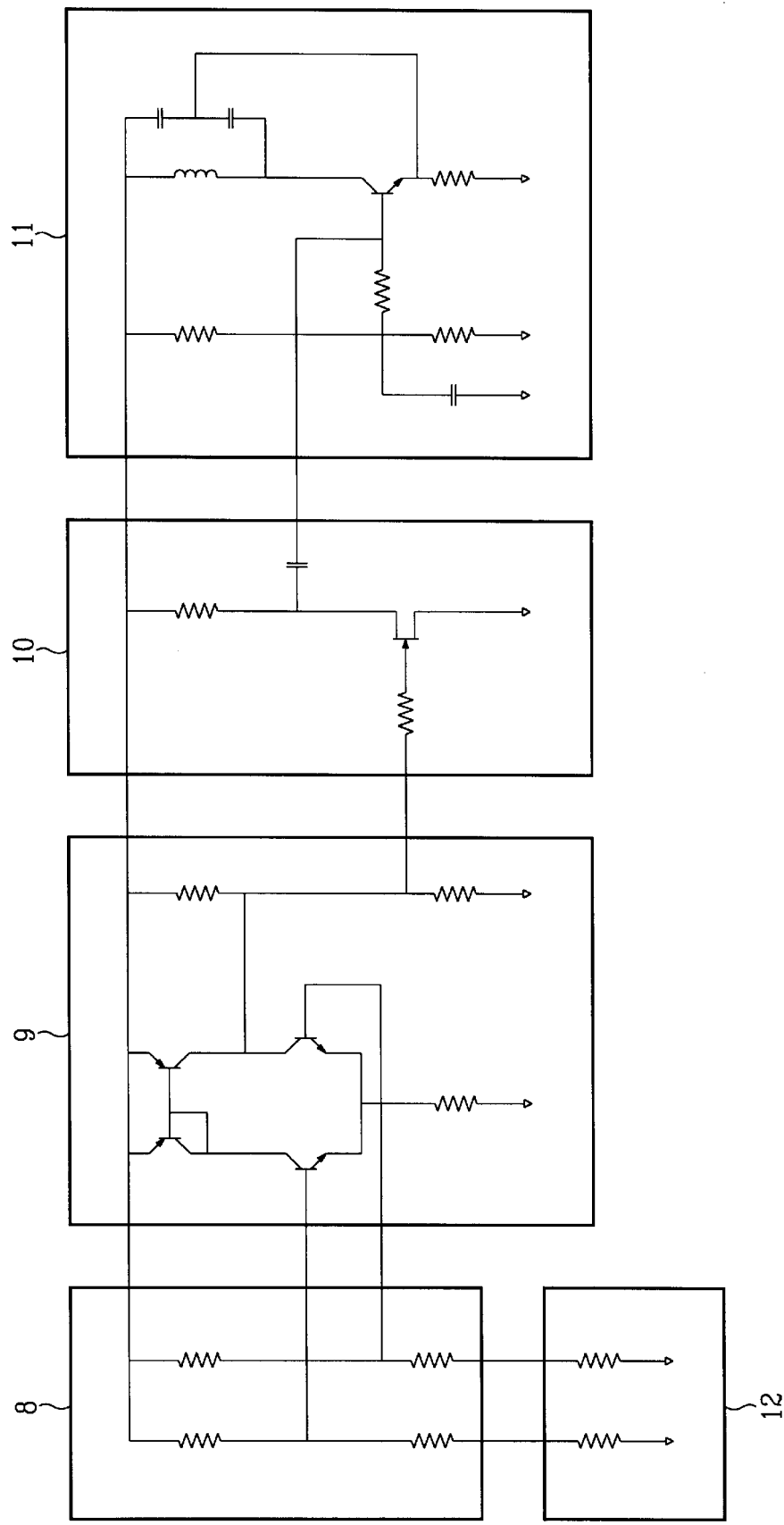
FIG. 2 is a circuit diagram (Circuit One) for use in the present invention.

FIG. 2 is an illustration of a circuit (Circuit One) for use in the invention. A pressure sensor (8) used in this example is a Piezoresistive Strain Gauge Bridge manufactured by Lucas Nova Sensor. However, other sensors may be used. Pressure changes to the sensor (8) produce changes in the sensor's output voltage. The sensor's output voltage is amplified by the Differential Amplifier (9) to provide a voltage input to a Frequency Modulator (10). The Modulator (10) shifts the frequency of a Colpitts Oscillator/Transmitter (11). A full-scale pressure swing (0–100 mm Hg) produces a +7% shift in the oscillator's frequency. The Colpitts Oscillator (11) in this case operates at a nominal frequency around 400–450 kHz. Other operating frequencies are easy to obtain by changing the value of the inductor (6). Since the inductor (6) is wound on the PMD (1) at the time of manufacture tuning is very easy. Offset Balance resistors (12) are used to zero out ambient pressure or, in other words, to calibrate the sensor (8) to output a signal corresponding to a known reference pressure.

Figure 3:
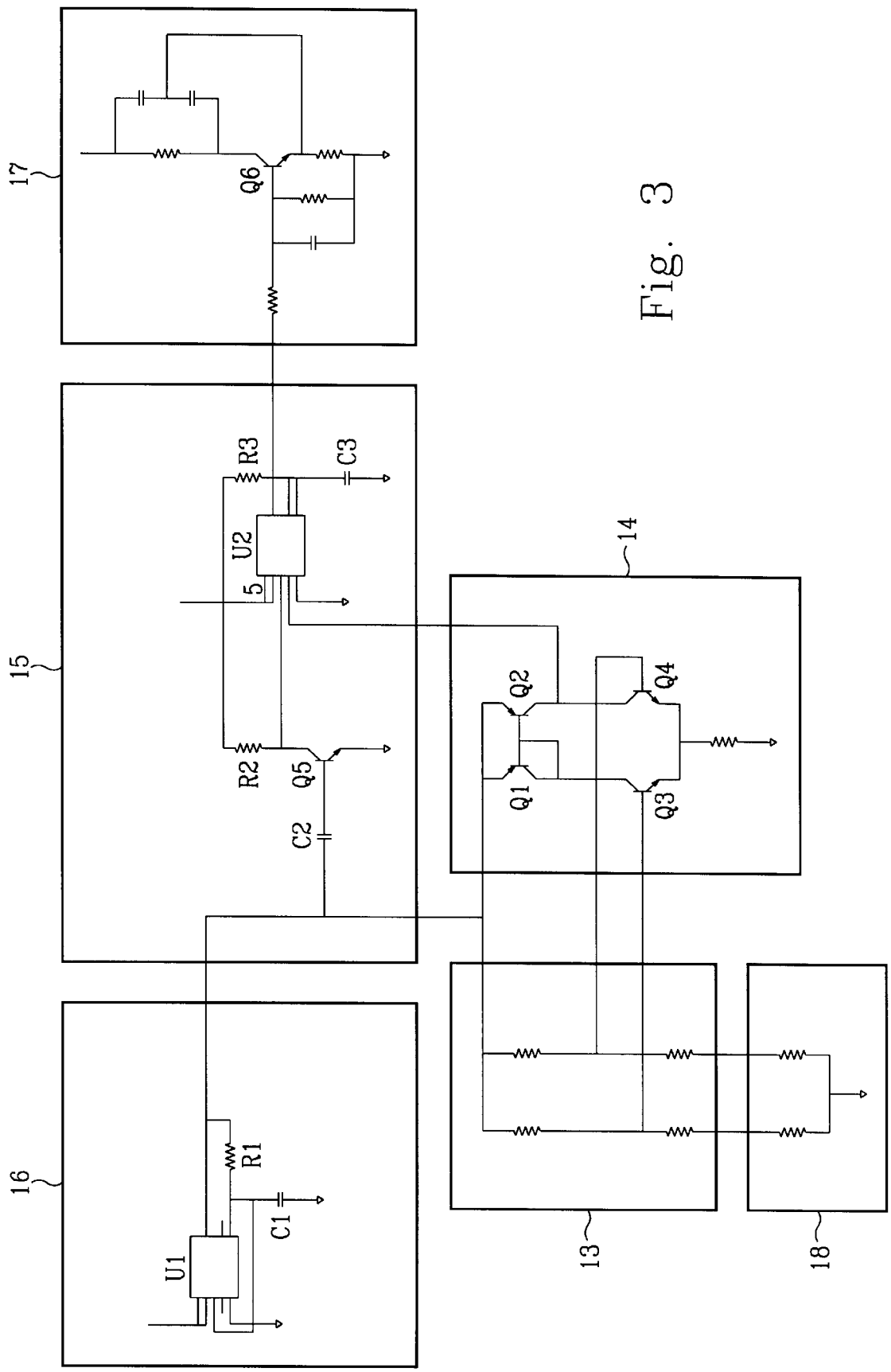
FIG. 3 is a circuit diagram (Circuit Two) for use in the present invention.

FIG. 3 is a circuit diagram (Circuit Two) for use in the present invention. The following abbreviations are used in this figure: C represents a capacitor; Q represents a transistor; R represents a resistor; and U represents an integrated circuit. A pressure sensor (13) used in this example is a Piezoresistive Strain Gauge Bridge manufactured by Lucas Nova Sensor. Pressure changes to the sensor (13) produce changes in the sensor's output voltage. The sensor's output voltage is amplified by a Transconductance Amplifier (14) to provide a control current input to a Pulse Width Modulator (PWM) (15). U1 produces a fixed period Clock (16) with a 50% duty cycle. This scheme reduces the power consumed by the sensor (13), amplifier (14) and PWM (15). When the output of U1 goes high, the sensor (13) and amplifier (14) begin operating and the output of the PWM (15) goes high turning on an Oscillator/Transmitter (17). The output of the PWM (15) returns low, shutting off the Oscillator/Transmitter (17) after a time defined by the R3 and C3 determined time constant and the voltage of U2 pin 5. Thus as the voltage of U2 pin 5 varies, the time of oscillator (17) shut off or transmitter pulse width varies. The output current of the transconductance amplifier (14) is fed into U2 pin 5. As the pressure increases on the sensor (13), the current from the transconductance amplifier (14) increases, raising the voltage on U2 pin 5 and increasing the width or duration of the transmitted pulse. When the output of U1 returns low, the sensor (13), amplifier (14) and PWM (15) are turned off. The oscillator (17) operates at a nominal frequency around 450 kHz. Other operating frequencies are easy to obtain by changing the value of the inductor (6). Since this inductor is wound on the PMD (1) at the time of manufacture tuning is very easy. Offset Balance resistors (18) are used to zero out ambient pressure or in other words to calibrate the sensor (13) to output a signal corresponding to a known reference pressure. Power consumption of this circuit is estimated to be 25% to 30% of that of Circuit One shown in FIG. 2.

Figure 4:
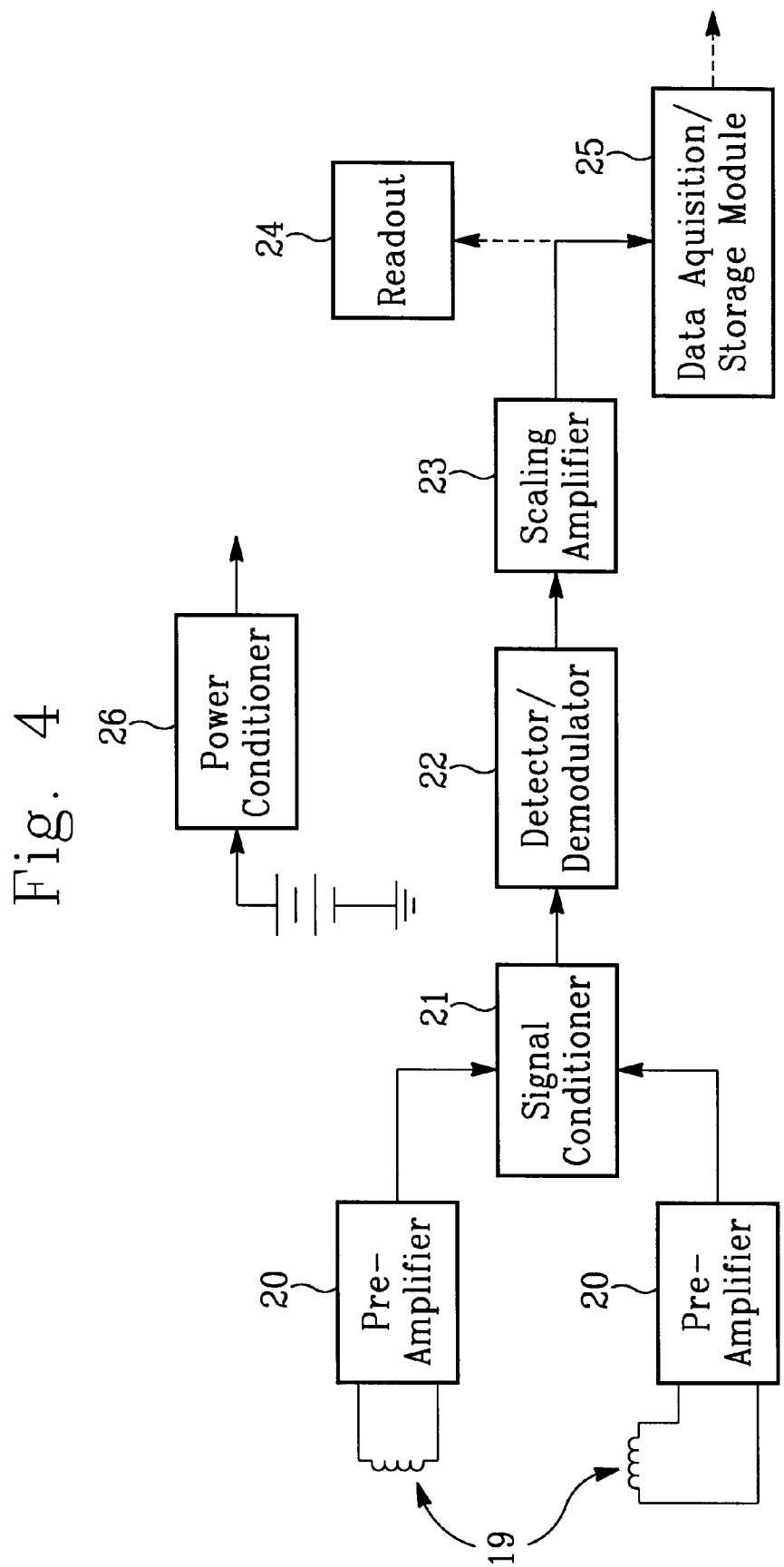
FIG. 4 is a block diagram of a receiver for use in the present invention.

FIG. 4 is a block diagram of a receiver for use in the present invention. The receiver includes at least one Receiving Antenna-Coil (19) connected to at least one Pre-Amplifier (20). The signal from the Pre-Amplifier (20) travels through a Signal Conditioner (21) to a Detector/Demodulator (22). The electronic signal further travels from the Detector/Demodulator (22) through a Scaling Amplifier (23) and is simultaneously distributed to a Readout (24) and a Data Acquisition/Storage Module (25). All circuits receive power which has first been routed through a Power Conditioner (26).

It will be understood that the above described embodiments of the present invention are susceptible to various modifications, changes, and adaptations, and the same are intended to be comprehended within the meaning and range of equivalents of the appended claims. As mentioned above, a multi-channel monitor can be employed and aspects of the bladder and/or urine other than pressure such as salinity, protein, sugar, etc., can be measured singly or in conjunction with each other. This would require modification of the sensor to sense for these properties.

Further, although a number of equivalent components may have been mentioned herein which could be used in place of the components illustrated and described with reference to the described embodiment, this is not meant to be an exhaustive treatment of all the possible equivalents, nor to limit the invention defined by the claims to any particular equivalent or combination thereof. A person skilled in the art would realize that there may be other equivalent components presently known, or to be developed, which could be used within the spirit and scope of the invention defined by the claims.

What Is claimed is:

1. A bladder monitor system comprising:
   a pressure measurement device capable of using magnetic induction telemetry, said measurement device further capable of being removably insertable into a bladder of an animal, said measurement device comprising:
   a. a self-contained device power source;
   b. a pressure sensor;
   c. at least one offset balance resistor operatively interconnected to said pressure sensor;
   d. a differential amplifier operatively interconnected to an output portion of said pressure sensor, said differential amplifier further operatively interconnected to a discharge portion of said self-contained device power source;
   e. a frequency modulator operatively interconnected to an output portion of said amplifier, said frequency modulator further operatively interconnected to said discharge portion of said self-contained device power source;
   f. an induction coil-antenna operatively interconnected to said discharge portion of said self-contained device power source;
   g. an oscillator operatively interconnected to said modulator, said oscillator further operatively interconnected to said induction coil antenna, said oscillator further operatively interconnected to said discharge portion of said self-contained device power source; and
   h. a telemetry circuit operatively interconnected to said pressure sensor, said telemetry circuit further operatively interconnected to said discharge portion of said self-contained device power source, said telemetry circuit further operatively interconnected to said induction coil antenna; and
   a receiver for receiving data from said pressure measurement device, said receiver comprising:
   a. a self-contained or external receiver power source;
   b. at least one pickup coil operatively interconnected to a discharge portion of said receiver power source;
   c. at least one preamplifier operatively interconnected to an output portion of said pickup coil, said preamplifier further operatively interconnected to said discharge portion of said receiver power source; and
   d. a signal conditioner operatively interconnected to an output portion of said preamplifier, said signal conditioner further operatively interconnected to said discharge portion of said receiver power source.

2. A bladder monitor system comprising:
   a pressure measurement device capable of using magnetic induction telemetry, said measurement device further capable of being removably insertable into a bladder of an animal; and
   a receiver for receiving data from said measurement device, said receiver comprising:
   a. a self-contained and/or external power source;
   b. at least one pickup coil operatively interconnected to a discharge portion of said power source;
   c. at least one preamplifier operatively interconnected to an output portion of said pickup coil, said preamplifier further operatively interconnected to said discharge portion of said power source;
   d. a signal conditioner operatively interconnected to an output portion of said preamplifier, said signal conditioner further operatively interconnected to said discharge portion of said power source;
   e. a detector operatively interconnected to an output portion of said signal conditioner, said detector further operatively interconnected to said discharge portion of said power source;
   f. a scaling amplifier, said scaling amplifier operatively interconnected to an output portion of said detector, said scaling amplifier further operatively interconnected to said discharge portion of said power source; and
   g. memory means for data acquisition and storage, said memory means operatively interconnected to said output portion of said readout circuit.

3. A bladder monitor system as in claim 1, wherein said pressure measurement device is coated with a biocompatible coating.

4. A bladder monitor system as in claim 1, wherein said self-contained device power source comprises at least one battery.

5. A bladder monitor system as in claim 1, wherein said pressure sensor is a piezoresistive sensor.

6. A bladder monitor system as in claim 2, wherein said detector comprises a demodulator.

7. A bladder monitor system as in claim 2, wherein said power source comprises at least one battery.

8. A bladder monitor system as in claim 2 further comprising:
   h. a readout circuit, said readout circuit operatively interconnected to an output portion of said scaling amplifier, said readout circuit further operatively interconnected to said discharge portion of said power source; and
   i. a readout display operatively interconnected to an output portion of said readout circuit, said readout display further operatively interconnected to said discharge portion of said power source.

9. A bladder monitor system as in claim 8, wherein said readout display comprises an alphanumeric readout display.

10. A bladder monitor system, comprising:
    a measurement device capable of using magnetic induction telemetry, said measurement device further capable of being removably insertable into a bladder of an animal, said measurement device comprising:
    a. a self-contained power source;
    b. a sensor;
    c. at least one offset balance resistor operatively interconnected to said sensor;
    d. a transconductance amplifier operatively interconnected to an output portion of said sensor, said transconductance amplifier further operatively interconnected to a discharge portion of said self-contained power source;
    e. a pulse width modulator operatively interconnected to an output portion of said transconductance amplifier, said pulse width modulator further operatively interconnected to said discharge portion of said self-contained power source;
    f. a clock operatively interconnected to said pulse width modulator, said clock further operatively interconnected to said sensor and said transconductance amplifier, said clock further operatively interconnected to said discharge portion of said self-contained power source; and
    g. an oscillator operatively interconnected to said pulse width modulator, said oscillator further operatively interconnected to said discharge portion of said self-contained power source.

11. A monitor system as in claim 10, wherein said measurement device is coated with a biocompatible coating.

12. A monitor system as in claim 10, wherein said self-contained power source comprises at least one battery.

13. A monitor system as in claim 10, wherein said sensor is a piezoresistive sensor.

14. A monitor system as in claim 13, wherein said sensor is a pressure sensor.

15. A method for determining urinary tract pressure in an animal comprising the steps of:
    a. inserting a pressure measurement device (PMD) into said animal's bladder or urinary tract;
    b. measuring said bladder or urinary tract pressure on said PMD; and
    c. removing said PMD from said animal's bladder or urinary tract.

16. A method as in claim 15 wherein said PMD comprises a pressure measurement device, said pressure measurement device comprising:
    a. a self-contained power source;
    b. a pressure sensor;
    c. at least one offset balance resistor operatively interconnected to said pressure sensor;
    d. a differential amplifier operatively interconnected to an output portion of said pressure sensor, said differential amplifier further operatively interconnected to a discharge portion of said self-contained power source;
    e. a frequency modulator operatively interconnected to an output portion of said differential amplifier, said frequency modulator further operatively interconnected to said discharge portion of said self-contained power source;
    f. an induction coil antenna, said induction coil antenna operatively interconnected to said discharge portion of said self-contained power source;
    g. an oscillator operatively interconnected to said frequency modulator, said oscillator further operatively interconnected to said induction coil antenna, said oscillator further operatively interconnected to said discharge portion of said self-contained power source; and
    h. a telemetry circuit operatively interconnected to said oscillator, said telemetry circuit further operatively interconnected to said pressure sensor, said telemetry circuit further operatively interconnected to said discharge portion of said self-contained power source.

17. A bladder monitor system comprising:
    a measurement device capable of using magnetic induction telemetry, said measurement device further capable of being removably insertable into a bladder of an animal, said measurement device comprising:
    a. a power source;

b. a sensor for sensing a biophysical aspect of the bladder; and
c. telemetry means, operatively connected to said power source and to said sensor, for telemetering a data signal received from said sensor; and a receiver, said receiver comprising:
  a. antenna means for receiving said data signal from said telemetry means;
  b. prearnplification means, operatively connected to said antenna means, for preamplifying said data signal; and
  c. signal conditioning means, operatively connected to said preamplification means, for conditioning said data signal.

\* \* \* \* \*